United States Patent [19]

Okada et al.

[11] Patent Number: 4,943,666
[45] Date of Patent: Jul. 24, 1990

[54] PROCESS FOR PRODUCING NITROPHENOL COMPOUND

[75] Inventors: Taiiti Okada, Kyoto; Toru Ishida, Kobe, both of Japan

[73] Assignee: Takeda Chemical Industries, Ltd., Osaka, Japan

[21] Appl. No.: 337,886

[22] Filed: Apr. 14, 1989

[30] Foreign Application Priority Data

Apr. 27, 1988 [JP] Japan ............................... 63-106147

[51] Int. Cl.$^5$ ..................... C07C 79/32; C07C 79/02
[52] U.S. Cl. ................................ 568/709; 568/713
[58] Field of Search ............................. 568/709, 713

[56] References Cited

U.S. PATENT DOCUMENTS

| | | | |
|---|---|---|---|
| 3,108,927 | 10/1963 | Pyne | 568/709 |
| 3,636,037 | 1/1972 | Donninger et al. | 568/709 |
| 4,038,328 | 6/1977 | Pelster | 568/709 |
| 4,723,043 | 2/1988 | Ratton | 568/709 |

FOREIGN PATENT DOCUMENTS 0777124  1/1968  Canada ............................ 568/709

OTHER PUBLICATIONS

Gasparic, Collection Czechoslov. Chem. Commun., 29(6), 1374–1379 (1964) with English Translation of abstract on p. 1374.

Gasparic, Z. Anal. Chem., 199(4), 276–290 (1964) with English Summary on p. 289.

Graham, "Journal of Chromatography", 33, 118–124 (1968).

Primary Examiner—Werren B. Lone
Attorney, Agent, or Firm—Wenderoth, Lind & Ponack

[57] ABSTRACT

An improved industrial process for producing a compound of the general formula:

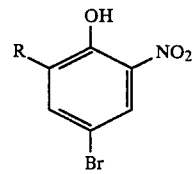

wherein R is an alkyl group having 1 to 4 carbon atoms which comprises reacting a compound of the general formula:

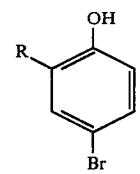

wherein R is as defined above with nitrous acid in a mixed solvent of water and a water-insoluble or slightly soluble organic solvent.

7 Claims, No Drawings

PROCESS FOR PRODUCING NITROPHENOL COMPOUND

FIELD OF THE INVENTION

The present invention relates to a process for producing a nitrophenol compound which is useful for a synthetic intermediate of a medicine having benzoxazine skeleton.

BACKGROUND OF THE INVENTION

In general, nitrophenol (mainly o- or p-isomer) has been hitherto obtained by reacting phenol with nitric acid in sulfuric acid medium [for example, U. Al-Obaidi and R. B. Moodie, J. Chem. Soc. Perkin Trans. II, 467 (1985)].

However, when this method is applied to a halogenated phenol compound, particularly a phenol compound substituted with bromine, substitution, isomerization, disproportionation and the like occur and the nitrated product becomes a mixture thereof with by-products such as isomers, debrominated products and the like, which results in a low yield.

Under these circumstances, in order to establish a process for producing a nitrophenol compound in a good yield with less by-products which is advantageous from the industrial viewpoint, the present inventors have intensively studied a method for nitrating a phenol compound to convert into a corresponding nitrophenol compound. As the result, it has been found that the objective nitrophenol compound can be obtained in a good yield by reacting a p-bromophenol compound with nitrous acid in a mixed solvent of water and water-insoluble or slightly soluble organic solvent. That is, according to the present inventors' knowledge, in such a nitration reaction, when a phenol compound is reacted with nitric acid in sulfuric acid medium according to a known method, the yield of the objective nitrophenol compound is low. However, it has been surprisingly found that a nitrophenol compound can be selectively produced in a high yield by reacting the phenol compound with nitrous acid in a mixed solvent of water and a water-insoluble or slightly soluble organic solvent.

Canadian Patent Specification No. 777,124 issued on Jan. 30, 1968 discloses that a 2,6-di-tertiary-alkylated 4-nitrophenol is obtained by causing diluted aqueous nitric acid to act on a solution of the corresponding di-tertiary-alkyl-phenol in a water-insoluble organic solvent, but there is no disclosure about the reaction of a p-bromophenol compound with nitrous acid in the specification.

In Collection Czechoslov. Chem. Commun. 29(6), 1374–1379 (1964) and Z. Anal. Chem., 199(4), 276–290 (1964), J. Gasparic discloses the reaction of o-bromophenol compound with nitrous acid in a slightly acidic medium, but does not disclose the use of a water-insoluble or slightly soluble organic solvent.

OBJECTS OF THE INVENTION

The main object of the present invention is to provide an improved industrial process for producing a nitrophenol compound.

This object as well as other objects and advantages of the present invention will become apparent to those skilled in the art from the following description.

SUMMARY OF THE INVENTION

According to the present invention, there is provided a process for producing a compound of the general formula:

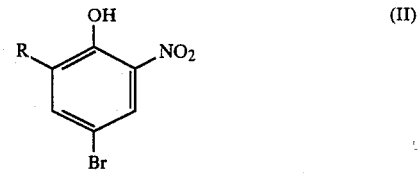

(II)

wherein R is an alkyl group having 1 to 4 carbon atoms which comprises reacting a compound of the general formula:

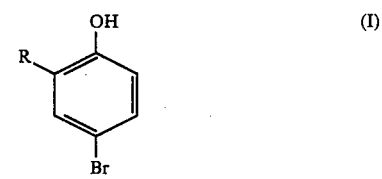

(I)

wherein R is as defined above with nitrous acid in a mixed solvent of water and water-insoluble or slightly soluble organic solvent.

DETAILED DESCRIPTION OF THE INVENTION

As the alkyl group represented by R in the phenol compound (I) used as the raw material of the present invention, there are straight-chain or branched groups having 1 to 4 carbon atoms such as methyl, ethyl, n-propyl, isopropyl, n-butyl, t-butyl and the like. These compounds are commercially available or they can be readily prepared from a commercially available raw material according to a known method.

The water-insoluble or slightly soluble organic solvent to be used is that having solubility in water of not more than 10% by weight and any of such a solvent can be used in so far as it does not hinder the nitration reaction of the present invention. Examples of the solvent includes aliphatic hydrocarbons such as hexane, heptane, nonane, decane, dodecane and the like, cyclic aliphatic hydrocarbons such as cyclohexane, methylcyclohexane, ethylcyclohexane, t-butylcyclohexane, 1,1-dimethylcyclohexane, 1,2-dimethylcyclohexane, propylcyclohexane, isopropylcyclohexane and the like, chlorinated aliphatic hydrocarbons such as carbon tetrachloride, chloroform, tetrachloroethylene, hexachloroethane, methylene chloride, dichloroethane, tetrachloroethane, trichloroethylene, 1-chlorobutane, 1,2-dichlorobutane and the like, ethers such as diethyl ether, diisopropyl ether and the like, and lower alkyl esters of aliphatic carboxylic acids such as ethyl acetate, propyl acetate, butyl acetate and the like. These organic solvents can be used alone or in combination thereof in any proportion, particularly, to use a mixture of n-hexane and isopropyl ether is preferred.

The process of the present invention is carried out in a two-phase system mixed solvent of water and the organic solvent. The mixing ratio of water and the organic solvent is appropriately selected. However, usually, a good yield can be obtained in the volume ratio of water: the organic solvent of 1:0.1 to 5, preferably, 1:0.5 to 1.

The process of the present invention is carried out by addition of a nitrite (e.g., an alkali metal salt of nitrous acid such as sodium nitrite, etc.) and an acid (e.g., sulfuric acid, hydrochloric acid, acetic acid, p-toluenesulfonic acid, trifluoroacetic acid, etc.) to a reaction system to form nitrous acid in the reaction system to effect nitration of the phenol compound (I) with nitrous acid. As the acid, it is preferred to use sulfuric acid. Usually, the nitrite is used in an amount of 2-fold mole or more, preferably 3-fold mole based on the phenol compound (I) and is used by dissolving it in 2 to 4-fold by volume of water (used as the water phase of the mixed solvent). It is preferred to use the acid in equal mole or more based on the phenol compound (I). Particularly, a good result can be obtained by addition thereof in 2 to 7-fold mole based on the phenol compound (I).

The order of the addition of the nitrite and the acid is not specifically limited. For example, the nitrite can be added to a mixture of the acid and the phenol compound (I) or, preferably, the acid can be added to a mixture of the nitrite and the phenol compound (I).

The reaction temperature and time are not specifically limited and they can be widely varied. For example, the objective nitrophenol compound (II) can be obtained in a high yield and a high purity by carrying out the reaction at −10° to 100° C., preferably, 0° to 40° C. for 20 minutes to 10 hours, preferably, 30 minutes to 3 hours.

The resulting nitrophenol compound (II) is isolated from the reaction system according to a known method such as solvent extraction, concentration, crystallization, recrysatllization, chromatography and the like and is used for synthesis of various kinds of medicines.

For example, according to the reaction scheme:

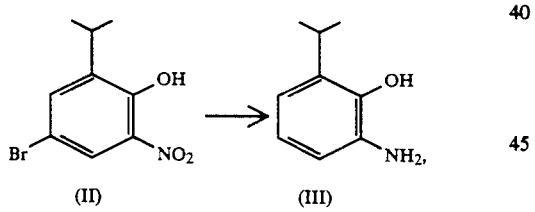

(II)    (III)

4-bromo-2-isopropyl-6-nitrophenol (II) is converted into 2-amino-6-isopropylphenol (III) by a known method and, according to the process described in EP-A-No. 0 234 018, this 2-amino-6-isopropylphenol can be converted into a benzoxazine derivative which is useful for a preventive or therapeutic agent for diabetic complication such as diabetic cataract, retinopathy, nephropathy, neurosis and the like.

The process of the present invention is extremely useful for an industrial manufacturing process because the objective nitrophenol compound can be obtained in high purity and high yield under gentle reaction conditions. As the results, in an industrial production of a final objective product by using the nitrophenol compound as a synthetic intermediate, the process of the present invention is very advantageous for production of the nitrophenol compound.

The following Examples and Reference Examples further illustrates the present invention in detail but are not to be construed to limit the scope thereof.

REFERENCE EXAMPLE 1

4-Bromo-2-isopropylphenol (I) (4.75 g) was dissolved in acetic acid (45 ml) and water (5 ml). Then, to the solution was added sulfuric acid (2 ml) and the solution was cooled to 0° C. Sodium nitrite (4.80 g) was dissolved in water (9.6 ml) and added dropwise to the above prepared solution at −3° to −1° C. over 50 minutes. After completion of the addition, the mixture was stirred at 15° C. for 10 minutes. To the mixture were added water (31 ml) and isopropyl ether (37 ml) and the mixture was stirred. Then, the isopropyl ether layer was separated. The isopropyl ether layer was washed in turn with water (31 ml), saturated aqueous sodium bicarbonate solution (31 ml×2) and water (31 ml). The isopropyl ether layer was concentrated under reduced pressure to obtain a red oil (5.55 g). The reaction can be illustrated by the following scheme:

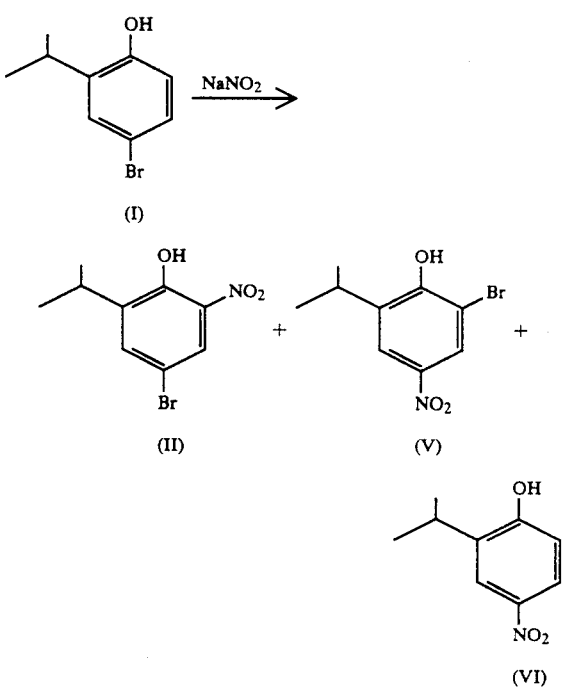

The above oil was subjected to column chromatography on silica gel (140 g) to isolate and purify the product. Among fractions firstly eluted with toluene, the fractions which showed one spot were collected and concentrated to obtain 4-bromo-2-isopropyl-6-nitrophenol (II) (3.57 g), yield: 62.0%. The product was dissolved in ethanol and treated with activated charcoal (50° C.) and the ethanol solution was then concentrated under reduced pressure to obtain a yellow oil. The oil was crystallized from n-hexane to obtain yellow crystals of 4-bromo-2-isopropyl-6-nitrophenol.

NMR (CDCl$_3$): δ1.26 (6H, doublet), 3.41 (1H, septet), 7.57 (1H, doublet), 8.09 (1H, doublet), 10.97 ppm (1H, singlet).

IR (liquid film): 1340, 1535 (NO$_2$), 3200 cm$^{-1}$ (OH).

Elemental Analysis for C$_9$H$_{10}$NO$_3$Br: Calcd: C, 41.56; H, 3.88; N, 5.39. Found: C, 41.33; H, 3.87; N, 5.62.

Among fractions subsequently eluted with toluene, the fractions which showed one spot were collected and concentrated to obtain 2-bromo-6-isopropyl-4-nitrophenol (V) (0.50 g), yield: 8.7%. The product was recrystallized from n-hexane to obtain yellow crystals.

NMR (CDCl$_3$) δ1.28 (6H, doublet), 3.37 (1H, septet), 6.25 (1H, broad singlet), 8.08 (1H, doublet), 8.27 ppm (1H, doublet).

IR (KBr): 1335, 1525 (NO$_2$), 3400 cm$^{-1}$ (OH).

Elemental Analysis for C$_9$H$_{10}$NO$_3$Br: Calcd: C, 41.56; H, 3.88; N, 5.39. Found: C, 41.53; H, 3.92; N, 5.41.

Then, among fractions eluted with methylene chloride, the fractions which showed one spot were collected and concentrated to obtain 2-isopropyl-4-nitrophenol (VI) (1.2 g), yield: 30.0%. The product was dissolved in ethanol and treated with active charcoal and then the solution was concentrated and recrystallized from n-hexane-toluene to obtain white crystals.

NMR (CDCl$_3$) δ1.29 (6H, doublet), 3.27 (1H, septet), 6.10 (1H, broad singlet), 6.85 (1H, doublet), 7.93–8.14 ppm (2H, multiplet).

IR (KBr): 1330, 1520 (NO$_2$), 3360 cm$^{-1}$ (OH).

Elemental Analysis for C$_9$H$_{11}$NO$_3$: Calcd: C, 59.66; H, 6.12; N, 7.73. Found: C, 59.72; H, 6.09; N, 7.69.

EXAMPLE 1

4-Bromo-2-isopropylphenol (I) (2.97 g) was dissolved in isopropyl ether (30 ml). To the solution was added a solution obtained by diluting 36% hydrochloric acid (8.46 g) with water (30 ml) and the resulting solution was cooled to about 3° C. Sodium nitrite (5.76 g) was dissolved in water (10 ml) and the solution was added dropwise to the above prepared solution at 2° to 4° C. over 20 minutes. After completion of the addition, the mixture was stirred at 20° C. for 60 minutes. Then, the isopropyl ether layer was separated and it was washed in turn with saturated aqueous sodium bicarbonate solution (31 ml) and water (31 ml). The isopropyl ether layer was concentrated under reduced pressure to obtain a red oil (3.27 g). As the result of analysis by high performance liquid chromatography, it was found that the oil was a mixture of 4-bromo-2-isopropyl-6-nitrophenol (II) (2.14 g, 59.6%) and 2-isopropyl-4-nitrophenol (VI) (0.61 g, 24.4%).

EXAMPLE 2

4-Bromo-2-isopropylphenol (I) (4.95 g) was dissolved in n-hexane (35 ml) and isopropyl ether (15 ml). To the solution was added 4.5 N sulfuric acid (50 ml) and the resulting solution was cooled to about 3° C. Sodium nitrite (4.81 g) was dissolved in water (15 ml) and the solution was added dropwise to the above prepared solution at 3° to 5° C. over 25 minutes. After completion of the addition, the mixture was stirred at 24° to 25° C. for 60 minutes. Then, to the solution were added n-hexane (35 ml), isopropyl ether (15 ml) and water (50 ml) and, after stirring, the organic layer was separated. The organic layer was washed in turn with water (50 ml×2), saturated aqueous sodium bicarbonate solution (50 ml) and water (50 ml ×2) and concentrated under reduced pressure to obtain a red oil (5.85 g). As the result of analysis by high performance liquid chromatography, it was found that the oil was a mixture of 4-bromo-2-isopropyl-6-nitrophenol (II) (5.3 g, 87.9%) and 2-isopropyl-4-nitrophenol (VI) (0.42 g, 9.9%).

EXAMPLE 3

4-Bromo-2-isopropylphenol (I) (2.97 g) was dissolved in n-hexane (30 ml). To the solution was added 2.4 N sulfuric acid (30 ml) and the resulting solution was cooled. Sodium nitrite (5.76 g) was dissolved in 2-fold by volume of water and the solution was added dropwise to the above prepared solution at 13° to 15° C. over 60 minutes. After completion of the addition, the mixture was stirred at 25° C. for 60 minutes. The organic layer was separated and it was washed according to the same manner as that described in Example 2 and concentrated under reduced pressure to obtain a red oil (3.02 g). As the result of analysis by high performance liquid chromatography, it was found that the oil was a mixture of 4-bromo-2-isopropyl-6-nitrophenol (II) (73.9%) and 2-isopropyl-4-nitrophenol (VI) (3.6%) which contained a trace amount of 2-bromo-6-isopropyl-4nitrophenol (V).

EXAMPLE 4

4-Bromo-2-isopropylphenol (I) (2.97 g) was dissolved in isopropyl ether (30 ml). To the solution was added 2.4 N sulfuric acid (30 ml) and the resulting solution was cooled. Sodium nitrite (5.76 g) was dissolved in 2-fold by volume of water and the solution was added dropwise to the above prepared solution at 3° to 25° C. After completion of the addition, the mixture was stirred at 25° C. for 90 minutes. The organic layer was separated and it was washed according to the same manner as that described in Example 2 and concentrated under reduced pressure to obtain a red oil (3.65 g). As the result of analysis by high performance liquid chromatography, it was found that the oil was a mixture of 4-bromo-2-isopropyl-6-nitrophenol (II) (66.3%) and 2-isopropyl-4-nitrophenol (VI) (30.0%) which contained a trace amount of 2-bromo-6-isopropyl-4-nitrophenol (V).

EXAMPLE 5

4-Bromo-2-isopropylphenol (I) (4.95 g) was dissolved in n-hexane (35 ml) and isopropyl ether (15 ml). To the solution was added 1.9 N sulfuric acid (50 ml) and the resulting solution was cooled. Sodium nitrite (4.81 g) was dissolved in 2-fold by volume of water and the solution was added dropwise to the above prepared solution at 3° to 5° C. over 50 minutes. After completion of the addition, the mixture was stirred at 25° C. for 60 minutes. Then, the organic layer was separated and it was washed according to the same manner as that described in Example 2 and concentrated under reduced pressure to obtain a red oil (5.15 g). As the result of analysis by high performance liquid chromatography, it was found that the oil was a mixture of 4-bromo-2-isopropyl-6-nitrophenol (II) (71.7%) and 2-isopropyl-4-nitrophenol (VI) (10.0%).

EXAMPLE 6

4-Bromo-2-isopropylphenol (I) (4.95 g) was dissolved in n-hexane (35 ml) and isopropyl ether (15 ml). To the solution was added 2.8 N sulfuric acid (50 ml) and the resulting solution was cooled. Sodium nitrite (8.01 g) was dissolved in 2-fold by volume of water and the solution was added dropwise to the above prepared solution at 3° C. over 30 minutes. After completion of the addition, when the mixture was heated to 25° C., the reaction was completed. Then, the organic layer was separated and it was washed according to the same manner as that described in Example 2 and concentrated under reduced pressure to obtain a red oil (5.74 g). As the result of analysis by high performance liquid chromatography, it was found that the oil was a mixture of 4-bromo-2-isopropyl-6-nitrophenol (II) (85.2%) and 2-isopropyl-4-nitrophenol (VI) (10.4%).

EXAMPLE 7

4-Bromo-2-isopropylphenol (I) (4.99 g) was dissolved in n-hexane (35 ml) and isopropyl ether (15 ml). To the solution was added 6.0 N sulfuric acid (50 ml) and the resulting solution was cooled. Sodium nitrite (4.81 g) was dissolved in 2-fold by volume of water and the solution was added dropwise to the above prepared solution at 3 to 5° C. over 23 minutes. After completion of the addition, the mixture was stirred at 24° C. for 30 minutes. Then, the organic layer was separated and it was washed according to the same manner as that described in Example 2 and concentrated under reduced pressure to obtain a red oil (5.68 g). As the result of analysis by high performance liquid chromatography, it was found that the oil was a mixture of 4-bromo-2-isopropyl-6-nitrophenol (II) (84.5%) and 2-isopropyl-4-nitrophenol (VI) (12.9%).

EXAMPLE 8

4-Bromo-2-isopropylphenol (I) (20.0 g) was dissolved in n-hexane (150 ml) and isopropyl ether (65 ml). Sodium nitrite (20.7 g) was dissolved in water (100 ml) and the solution was added to the above prepared solution. 4.5 N Sulfuric acid (215 ml) was added dropwise to the mixture at 25° C. over 150 minutes. After completion of the addition, the mixture was stirred at 25° C. for 90 minutes and the organic layer was separated. The organic layer was washed in turn with water (215 ml), saturated aqueous sodium bicarbonate solution (215 ml) and water (215 ml) and concentrated under reduced pressure to obtain a red oil (25.55 g). As the result of analysis by high performance liquid chromatography, it was found that the oil was a mixture of 4-bromo-2-isopropyl-6-nitrophenol (II) (22.38 g, 92.5%) and 2-isopropyl-4-nitrophenol (VI) (0.65 g, 3.9%).

EXAMPLE 9

4-Bromo-2-isopropylphenol (I) (20.0 g) was dissolved in n-hexane (150 ml) and isopropyl ether (65 ml). Sodium nitrite (20.7 g) was dissolved in water (100 ml) and the solution was added to the above prepared solution. 4.5 N Sulfuric acid (215 ml) was added dropwise to the mixture at 25° C. over 270 minutes. After completion of the addition, the mixture was stirred at 25° C. for 150 minutes and the organic layer was separated. The organic layer was washed in turn with water (215 ml), saturated aqueous sodium bicarbonate solution (215 ml) and water (215 ml) and concentrated under reduced pressure to obtain a red oil (24.93 g). As the result of analysis by high performance liquid chromatography, it was found that the oil was a mixture of 4-bromo-2-isopropyl-6-nitrophenol (II) (22.69 g, 93.8%) and 2-isopropyl-4-nitrophenol (VI) (0.67 g, 4.0%).

REFERENCE EXAMPLE 2

4-Bromo-2-isopropylphenol (I) (4.75 g) was dissolved in acetic acid (90 ml). To the solution was added sulfuric acid (3.68 g) and the resulting solution was cooled. Sodium nitrite (4.80 g) was dissolved in water (10 ml) and the solution was added dropwise to the above prepared solution at 0° to 1° C. over 60 minutes. The layers were separated and, according to the same manner as that described in Reference Example 1, extraction with isopropyl ether and washing were carried out. Then, the isopropyl ether layer was concentrated under reduced pressure to obtain a red oil (5.53 g). As the result of analysis by high performance liquid chromatography, it was found that the product was a mixture of 4-bromo-2-isopropyl-6-nitrophenyl nitrophenyl (II) (64.7%), 2-bromo-6-isopropyl-4-nitrophenol (V) (12.2%) and 2-isopropyl-4-nitrophenol (VI) (27.5%).

REFERENCE EXAMPLE 3

4-Bromo-2-isopropylphenol (I) (4.75 g) was dissolved in acetic acid (25 ml). To the solution was added sulfuric acid (3.68 g) and the resulting solution was cooled. Sodium nitrite (4.80 g) was dissolved in water (25 ml) and the solution was added dropwise to the above prepared solution at 0° to 2° C. over 20 minutes. After completion of the addition, the mixture was stirred at 10° C. for 20 minutes. After carrying out extraction with isopropyl ether and washing according to the same manner as that described in Reference Example 1, the isopropyl ether layer was concentrated under reduced pressure to obtain a red oil (5.36 g). As the result of analysis by high performance liquid chromatography, it was found that the product was a mixture of 4-bromo-2-isopropyl-6-nitrophenol (II) (52.5%), 2-bromo-6-isopropyl-4-nitrophenol (V) (7.0%) and 2-isopropyl-4-nitrophenol (VI) (37.5%).

REFERENCE EXAMPLE 4

4-Bromo-2-isopropylphenol (I) (4.64 g) was dissolved in acetic acid (45 ml). To the solution was added hydrochloric acid (5.23 g). Sodium nitrite (4.80 g) was dissolved in water (5 ml) and the solution was added dropwise to the above prepared solution at −2° to 2° C. over 55 minutes. After completion of the addition, the mixture was stirred at 10° C. for 60 minutes. After carrying out extraction with isopropyl ether and washing according to the same manner as that described in Reference Example 1, the isopropyl ether layer was concentrated under reduced pressure to obtain a red oil (5.40 g). As the result of analysis by high performance liquid chromatography, it was found that the product was a mixture of 4-bromo-2-isopropyl-6-nitrophenol (II) (55.3%), 2-bromo-6-isopropyl-4-nitrophenol (V) (21.4%) and 2-isopropyl-4-nitrophenol (VI) (18.0 %).

REFERENCE EXAMPLE 5

4-Bromo-2-isopropylphenol (I) (4.75 g) was dissolved in acetic acid (20 ml) and methylene chloride (20 ml) and the solution was cooled to 1° C. To the solution was added dropwise nitric acid (2.88 g, content: 61%) at 1° to 3° C. over 40 minutes. After completion of the addition, the mixture was stirred at 1° to 3° C. for 10 minutes. Then, to the mixture was added methylene chloride (30 ml) and water (30 ml). After stirring the mixture, the methylene chloride layer was separated. The methylene chloride layer was washed in turn with saturated aqueous sodium bicarbonate solution (80 ml×2) and water (80 ml). The methylene chloride layer was concentrated under reduced pressure to obtain a red oil (5.58 g). As the result of analysis by high performance liquid chromatography, it was found that the oil was found a mixture of 4-bromo-2-isopropyl-6-nitrophenol (II) (3.14 g, 54.7%) and 2-bromo-6-isopropyl-4-nitrophenol (V) (1.17 g, 20.4%).

REFERENCE EXAMPLE 6

4-Bromo-2-isopropylphenol (I) (4.75 g) was dissolved in acetic acid (20 ml) and methylene chloride (20 ml) and the solution was cooled to −7° C. Nitric acid (2.88 g, content: 61%) was dissolved in acetic acid (5 ml) and methylene chloride (5 ml) and the solution was added dropwise to the above prepared solution at −7° to 0° C. over 60 minutes. After completion of the addition, the mixture was stirred at about 0° C. for 10 minutes. Then, to the mixture were added methylene chloride (30 ml) and water (30 ml) and the methylene chloride layer was separated. The methylene chloride layer was washed in turn with saturated aqueous sodium bicarbonate solution (80 ml x 2) and water (80 ml). The methylene chloride layer was concentrated under reduced pressure to obtain a red oil (5.36 g). As the result of analysis by high performance liquid chromatography, it was found that the oil was a mixture of 4-bromo-2-isopropyl-6-nitrophenol (II) (2.64 g, 46.1%) and 2-bromo-6-isopropyl-4-nitrophenol (V) (0.95 g, 16.6%).

REFERENCE EXAMPLE 7

4-Bromo-2-isopropyl-6-nitrophenol (63.1 g) was dissolved in methanol (442 ml) and to the solution was added 5% Pd-C (11.0 g, water content: 50%). The mixture was subjected to catalytic reduction for 2.5 hours with bubbling hydrogen at hydrogen pressure of 1 to 2 kg/cm² with maintaining the external temperature at about 25° C. After completion of the reaction, Pd-C was filtered off and the filtrate was concentrated under reduced pressure at an external temperature of not more than 70° C. Then, the residue was washed with ethyl acetate (200 ml) and dried to obtain 2-amino-6-isopropylphenol hydrobromide (23.0 g, 40.8%). The product was recrystallized from methanoldiethyl ether to obtain colorless plates, m.p. 210°–213° C. (decomp.).

NMR (d$_6$-DMSO): δ1.17 (6H, doublet), 3.37 (1H, septet), 6.80–7.30 (3H, multiplet), 9.43 ppm (3H, broad absorption).

Elemental Analysis for C$_9$H$_{13}$NO.HBr: Calcd: C, 46.57; H, 6.08; N, 6.03 Found: C, 46.66; H, 6.14; N, 6.02.

What is claimed is:

1. A process for producing a compound of the formula:

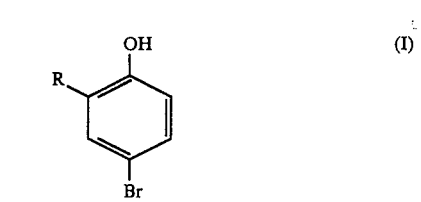

wherein R is an alkyl group having 1 to 4 carbon atoms which comprises reacting a compound of the formula:

(I)

wherein R is as defined above with nitrous acid at −10° to 100° C. in a mixed solvent of water and a water-insoluble or slightly soluble organic solvent having a water solubility of not more than 10% by weight.

2. The process according to claim 1, wherein the volume ratio of water: the organic solvent is 1:0.1 5.

3. The process according to claim 1, wherein nitrous acid is formed in a reaction system by reaction of an alkali metal salt of nitrous acid with an acid selected from the group consisting of sulfuric acid, hydrochloric acid, p-toluenesulfonic acid and trifluoroacetic acid.

4. The process according to claim 3, wherein the nitrite is added to a mixture of the compound (I) and the acid.

5. The process according to claim 3, wherein the acid is added to a mixture of the compound (I) and the nitrite.

6. The process according to claim 4, wherein the nitrite is sodium nitrite.

7. The process according to claim 3, wherein the acid is sulfuric acid.

* * * * *